United States Patent [19]

Williams

[11] Plant 4,305

[45] Sep. 19, 1978

[54] MINIATURE ROSE PLANT

[76] Inventor: Ernest D. Williams, 1510 Lebanon Ave., Dallas, Tex. 75208

[21] Appl. No.: 791,637

[22] Filed: Apr. 27, 1977

[51] Int. Cl.[2] ..... A01H 5/00

[52] U.S. Cl. ..... Plt./7

[58] Field of Search ..... Plt./7

*Primary Examiner*—Robert E. Bagwill

*Assistant Examiner*—James R. Feyrer

[57] ABSTRACT

The subject of the present invention is a new and distinct variety of miniature rose plant of the miniature class resembling the variety Over The Rainbow (U.S. Plant Pat. No. 3,472) but differing especially in the brillance of its orange color and the contrasting light color of the reverse side of petals.

1 Drawing Figure

The present invention relates to a new and distinct variety of hardy, dwarf, bush type rose plant of the miniature class: the variety being primarily characterized — as to novelty — by bright orange color with light yellow to cream reverse, the general color effect being similar to Over The Rainbow (U.S. Plant Pat. No. 3,472).

The variety is further characterized by:

An abundance of bloom with flowers borne singly or several to stem in loose clusters.

Little or no fragrance.

A plant which is vigorous, of rounded spreading shape and with semi-glossy, medium-small foliage with pointed leaflets; the buds and flowers being similar in form and size to Over The Rainbow.

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between an unnamed orange color floribunda seedling (not patented) as the seed parent and Over The Rainbow (miniature — U.S. Plant Pat. No. 3,472) as the pollen parent.

Subsequent to origination of the variety it was successfully asexually reproduced by cuttings in my nursery located as aforesaid and at Sequoia Nursery, Visalia, Calif., the reproductions having run true in all respects.

The color photograph illustrates the variety, including foliage, buds and flowers. Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; seedling; greenhouse; outdoors; cut flowers; garden decoration; potted plant.

Class: Miniature. Variety name 'Gloriglo'.

Flowers: Continuity; continuous — repeat bloom all season. Fragrance; little or none.

Flowers borne: Singly and several together (three to five) on sturdy, wirey, medium length stems.

Quantity of bloom: Abundant both outside and in greenhouse.

Bud: Peduncle — medium length; slender but sturdy; erect; medium green, sometimes tinted bronze (outdoors); hairs — few. Before calyx breaks; size — small. Form: medium long, inverted cone shape; pointed with several foliaceous appendages and few or no hairs on surface of bud; with foliaceous parts extending beyond the tip of the bud equal to one-half or more of its length. Color — medium green, occasionally tinted with bronze (outdoors). As calyx breaks, color — yellowish blending into pinkish orange color on upper portion; opens: well in all weather. Size — small.

Bloom: Size when fully open — small, averaging about 35 to 38 mm(1½"). Petalage — double — average about 35 petals arranged regularly. Form — full; high center at first, becoming more open in the center, with petals rolled loosely outward, and later at maturity open, with petals slightly folded downward at edges and rolled loosely outward and downward. Open flowers often show yellow stamens.

Petals: Thick; satiny on inside and on outside surface. Shape — outside petals, broad lanceolate with rounded tip; intermediate — broad lanceloate with rounded tip; inside — lanceolate with rounded or small acute tip.

Color: Newly opened flower from a plant grown outdoors September, 1975, Dallas, Tex.

*Outside petal.*—Outside surface — near Poppy Red 16/3 blending with yellow toward base; inside surface — near Mandarin Red 17 with base of petal yellow.

*Intermediate petal.*—Outside surface — similar to outside petal. Inside surface — similar to outside petal, but lower ⅓ of petal is cream to light yellow.

*Inner petal.*—Outside surface — same as intermediate petal; inside surface — same as intermediate petal. General color effect newly opened flowers — bright orange to orange red. Three days open — color; upper surface similar to newly opened flowers but slightly lighter shade; reverse side — similar to freshly opened flower but more white. Behavior — spent petals drop off. Flower longevity (October 1976) — plant in pot 5–7 days or longer. Cut flowers at living room temperature 4–7 days.

Reproductive organs:

*Stamens.*—moderate number, arranged regularly about pistil.

*Filaments.*—Varying length, light yellow.

*Anthers.*—Well formed; yellow.

*Pollen.*—Fair amount.

*Pistils.*—Average number.

*Styles.*—Fairly even; short to medium length; bunched; color — reddish.

*Stigma.*—Yellowish.

*Ovaries.*—All enclosed in calyx.

*Hips.*—Few or none.

*Sepals.*—Permanent; spear shaped; recurved.

*Seed.*—Few or none.

Foliage:

*Leaves.*—Compound of five (sometimes three or seven) leaflets — shape: broad lanceolate, nearly oval; apex acute; base rounded. Margin serrate. Color: medium green; new growth — reddish. Rachis: Medium strength; upperside may have few tiny short prickles, grooved; underside sparsely thorny with few or no tiny prickles. Stipules: Medium long; medium width, medium length narrow points which turn out usually at about 45° or more.

Growth:

*Habit.*—Dwarf; busy; spreading; much branched.

*Growth.*—Free vigorous.

*Main stems.*—Color: medium to deep green.

*Thorns.*—Generally sparse. Fairly large, nearly straight, inclined slightly downward; color: brown. Prickles — none. Hairs — none.

*Branches.*—Color: medium green. Thorns: sparse; medium length; slender; nearly straight; inclined slightly downward. Color: brown. Medium to short oval base. Prickles: none. Hairs: none.

*New shoots.*—Color: reddish. Thorns: sparse; color; reddish; straight. Prickles — none. Hairs — none.

The miniature rose plant and its flowers as herein described may vary in slight detail due to climatic, soil and cultural conditions under which the variety may be grown; the present description being of the variety as grown at Visalia, Calif.

I claim:

1. A new and distinct variety of miniature rose plant of hardy, dwarf, bushy, much branched habit, essentially as illustrated and described, characterized by buds and flowers resembling the miniature rose 'Over The Rainbow' in size and color effect, but the present variety being more brilliantly orange color on top side of petals and the reverse side of petals being light yellow to near white; and further characterized by flowers of symmetrical form with excellent lasting quality both on the plant and as cut flowers; the variety is also characterized by a vigorous, healthy plant, easily propagated from cuttings, which flowers almost continuously during the growing season.

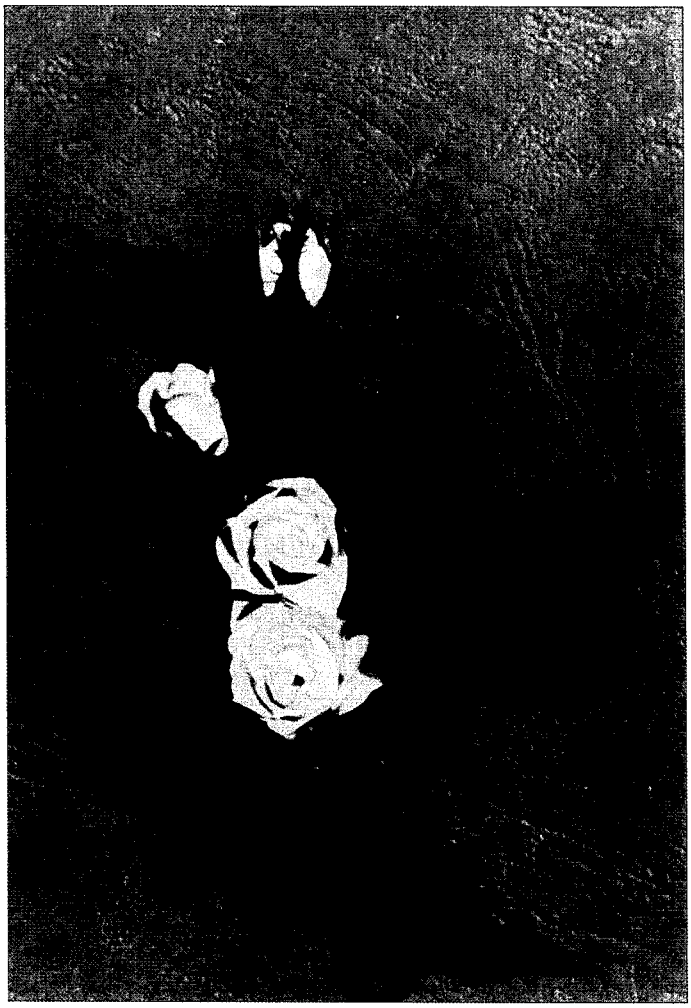

* * * * *